(12) United States Patent
Saurat

(10) Patent No.: US 9,011,885 B2
(45) Date of Patent: Apr. 21, 2015

(54) METHOD OF TREATING ACNE

(71) Applicant: Thesan Pharmaceuticals, Inc., Carlsbad, CA (US)

(72) Inventor: Jean Hilaire Saurat, Geneva (CH)

(73) Assignee: Thesan Pharmaceuticals, Inc., San Clemente, CA (US)

( * ) Notice: Subject to any disclaimer, the term of this patent is extended or adjusted under 35 U.S.C. 154(b) by 0 days.

(21) Appl. No.: 14/447,434

(22) Filed: Jul. 30, 2014

(65) Prior Publication Data

US 2015/0005373 A1   Jan. 1, 2015

Related U.S. Application Data

(63) Continuation of application No. 12/863,251, filed as application No. PCT/IB2009/050271 on Jan. 23, 2009, now abandoned.

(30) Foreign Application Priority Data

Jan. 23, 2008 (EP) .................................... 08150554

(51) Int. Cl.
| | | |
|---|---|---|
| A61K 9/00 | (2006.01) | |
| A61K 31/00 | (2006.01) | |
| A61K 31/407 | (2006.01) | |
| A61K 31/352 | (2006.01) | |

(52) U.S. Cl.
CPC .............. *A61K 9/0014* (2013.01); *A61K 31/00* (2013.01); *A61K 31/407* (2013.01); *A61K 31/352* (2013.01)

(58) Field of Classification Search
USPC ........................................................ 424/400
See application file for complete search history.

(56) References Cited

U.S. PATENT DOCUMENTS

| | | | |
|---|---|---|---|
| 6,555,573 B2 | 4/2003 | Rosenbloom | |
| 2003/0166583 A1 | 9/2003 | Yoa-Pu Hu et al. | |
| 2009/0028804 A1 | 1/2009 | Krutmann et al. | |

FOREIGN PATENT DOCUMENTS

| | | |
|---|---|---|
| CN | 101 953 838 A | 1/2011 |
| DE | 10 2006 011747 A1 | 9/2007 |
| EP | 1 138 323 A | 10/2001 |
| WO | WO 03/068742 A1 | 8/2003 |
| WO | WO 2004/041758 A1 | 5/2004 |
| WO | WO 2005/027867 A1 | 3/2005 |
| WO | WO 2007/060256 A2 | 5/2007 |
| WO | WO 2007/110241 A1 | 10/2007 |
| WO | WO 2007/060256 A3 | 11/2007 |
| WO | WO 2007/128723 A1 | 11/2007 |
| WO | WO 2007/128725 A1 | 11/2007 |
| WO | WO 2009/017369 A1 | 2/2009 |
| WO | WO 2009/093207 A1 | 7/2009 |
| WO | WO 2013/171696 A1 | 11/2013 |

OTHER PUBLICATIONS

Raza (J Invest Dermatol. Feb. 1992;98(2):233-40).*
Wattenberg (Cancer Res 1970;30:1922-1925).*
G. Gaitanis et al.: AhR Ligands, Malasezzin, and Indolo[3,2-b]Carbazole are Selectively Produced by *Malasezzin furfur* Strains Isolated from Seborrheic Dermatitis, *The Society for Investigative Dermatology*, 2008, vol. 128, pp. 1620-1625.
E. Fritsche et al.: "Lightening up the UV response by identification of the arylhydrocarbon receptor as a cytoplasmatic target for ultraviolet B radiation", *PNAS*, May 22, 2007, vol. 104, No. 21, pp. 8854-8856.
Search Report issued by the European Patent Office on Jun. 17, 2008 in connection with European Patent Application No. EP 08150554.
S. M. Puhvel et al.: "Effect of 2,3,7,8-Tetrachloro dibenzo-p-Dioxin on Murine Skin", *The Society for Investigative Dermatology, Inc.*, vol. 90, No. 3, Mar. 1988, pp. 354-358.
S.D. Seidel et al.: "Ah Receptor-Based Chemical Screening Bioassays: Application and Limitations for the Detection of Ah Receptor Agonists", *Toxicological Sciences*, 55, 2000, pp. 107-115.
Y.D. Wei et al.: "Rapid and transient induction of CYP1A1 gene expression in human cells by the tryptophan photoproduct 6-formylindolo[3,2-b]carbazole", *Chemico-Biological Interactions*, 110, 1998, pp. 39-55.
M. Mukai et al.: "Effects of Tryptophan Photoproducts in the Circadian Timing System: Searching for a Physiological Role for Aryl Hydrocarbon Receptor", *Toxicological Sciences*, 95(1), 2007, pp. 172-181.
J.M. Rowe et al.: "Illuminating Role of CYP1A1 in Skin Function", *The Journal of Investigative Dermatology*, vol. 128, No. 7, Jul. 2008, pp. 1866-1868.
Non-Final Office Action issued, by the U.S. Patent and Trademark Office on Feb. 24, 2012 in connection with U.S. Appl. No. 12/863,251.

(Continued)

*Primary Examiner* — Peter J Reddig
*Assistant Examiner* — Devang Thakor
(74) *Attorney, Agent, or Firm* — John P. White; Cooper & Dunham LLP

(57) ABSTRACT

The use, as a dermatological or cosmetic medicament, of compounds capable of transiently interacting with the AhR receptor (aryl hydrocarbon receptor) as agents for modulating skin functions such as sebaceous function, skin healing, skin atrophy termed "dermatoporosis", estrogen deprivation and defense against infection, without inducing other toxic effects of the TCDD type.

The compounds that interact with the AhR receptor are chosen in that they have a metabolism favorable to the dissociation of these effects, in particular by virtue of in situ production from a precursor and/or metabolization modulated in situ.

4 Claims, 20 Drawing Sheets

(56) References Cited

OTHER PUBLICATIONS

Response to Feb. 24, 2012 Office Action filed with the U.S. Patent and Trademark Office on Jul. 24, 2012 in connection with U.S. Appl. No. 12/863,251.
Notice of Non-Compliant Amendment issued by the U.S. Patent and Trademark Office on Jul. 27, 2012 in connection with U.S. Appl. No. 12/863,251.
Response to Notice of Non-Compliant Amendment filed with the U.S. Patent and Trademark Office on Aug. 7, 2012 in connection with U.S. Appl. No. 12/863,251.
Final Office Action issued by the U.S. Patent and Trademark Office on Nov. 16, 2012 in connection with U.S. Appl. No. 12/863,251.
Response to Final Office Action and Request for Continued Examination filed with the U.S. Patent and Trademark Office on Apr. 16, 2013 in connection with U.S. Appl. No. 12/863,251.
Non-Final Office Action issued by the U.S. Patent and Trademark Office on Jun. 11, 2014 in connection with U.S. Appl. No. 12/863,251.
Voluntary Amendment filed with the European Patent Office on Oct. 25, 2010 in connection with European Patent Application No. 09703782.4.
International Search Report issued by the International Searching Authority on May 13, 2009 in connection with PCT International Application No. PCT/IB2009/050271.
Written Opinion of the International Searching Authority issued by the International Searching Authority on Oct. 4, 2010 in connection with PCT International Application No. PCT/IB2009/050271.
International Preliminary Report on Patentability issued by the International Bureau of WIPO on Oct. 5, 2010 in connection with PCT International Application No. PCT/IB2009/050271.
International Search Report issued by the International Searching Authority on Aug. 14, 2013 in connection with PCT International Application No. PCT/IB2013/053979.

\* cited by examiner

FIG. 4B

| Genbank | Gene Symbol | Description | mean FC |
|---|---|---|---|
| BE856376 | ACSBG1 | acyl-CoA synthetase bubblegum family member 1 | -32.62 |
| AB014531 | ACSBG1 | acyl-CoA synthetase bubblegum family member 1 | -7.68 |
| D16350 | ACSM3 | acyl-CoA synthetase medium-chain family member 3 | -14.29 |
| NM_005622 | ACSM3 | acyl-CoA synthetase medium-chain family member 3 | -10.34 |
| AF468053 | ALOX15B | arachidonate 15-lipoxygenase, second type | -39.89 |
| NM_001141 | ALOX15B | arachidonate 15-lipoxygenase, second type | -41.53 |
| AB048286 | DGAT2 | diacylglycerol O-acyltransferase homolog 2 (mouse) : diacylglycerol O-acyltransferase homolog 2 (mouse) | -8.23 |
| AW469523 | DGAT2 | diacylglycerol O-acyltransferase homolog 2 (mouse) | -9.73 |
| BC039181 | DGAT2L3 | diacylglycerol O-acyltransferase 2-like 3 | -40.77 |
| AF292387 | ELOVL3 | elongation of very long chain fatty acids (FEN1/Elo2, SUR4/Elo3, yeast)-like 3 | -108.49 |
| AL136939 | ELOVL5 | ELOVL family member 5, elongation of long chain fatty acids (FEN1/Elo2, SUR4/Elo3-like, yeast) | -4.29 |
| BF973387 | ELOVL5 | ELOVL family member 5, elongation of long chain fatty acids (FEN1/Elo2, SUR4/Elo3-like, yeast) | -4.11 |
| AC004685 | FA2H | fatty acid 2-hydroxylase | -4.72 |
| NM_024306 | FA2H | fatty acid 2-hydroxylase | -24.38 |
| NM_001446 | FABP7 | fatty acid binding protein 7, brain | -17.33 |
| NM_001446 | FABP7 | fatty acid binding protein 7, brain | -16.77 |
| BE540552 | FADS1 | fatty acid desaturase 1 | -15.40 |
| BG165833 | FADS1 | fatty acid desaturase 1 | -12.75 |
| AL512760 | FADS1 | fatty acid desaturase 1 | -10.88 |
| NM_004265 | FADS2 | fatty acid desaturase 2 | -21.97 |
| AA872727 | FDFT1 | farnesyl-diphosphate farnesyltransferase 1 | -2.19 |
| BC003573 | FDFT1 | farnesyl-diphosphate farnesyltransferase 1 | -2.99 |
| NM_002130 | HMGCS1 | 3-hydroxy-3-methylglutaryl-Coenzyme A synthase 1 (soluble) | -11.44 |
| BG035985 | HMGCS1 | 3-hydroxy-3-methylglutaryl-Coenzyme A synthase 1 (soluble) | -4.44 |
| NM_000662 | HSD3B1 | hydroxy-delta-5-steroid dehydrogenase, 3 beta- and steroid delta-isomerase 1 | -109.31 |
| NM_058165 | MOGAT1 | monoacylglycerol O-acyltransferase 1 | -7.18 |
| AK000245 | MOGAT2 | monoacylglycerol O-acyltransferase 2 | -8.34 |
| NM_002888 | RARRES1 | retinoic acid receptor responder (tazarotene induced) 1 | -6.58 |
| AI669229 | RARRES1 | retinoic acid receptor responder (tazarotene induced) 1 | -12.12 |
| NM_002888 | RARRES1 | retinoic acid receptor responder (tazarotene induced) 1 | -13.22 |
| L21934 | SOAT1 | sterol O-acyltransferase (acyl-Coenzyme A: cholesterol acyltransferase) 1 | -18.15 |

FIG. 4C

| | | | |
|---|---|---|---|
| | -7.54 | | |
| | -9.19 | | |
| | -6.71 | | |
| | -17.53 | | |

| | | |
|---|---|---|
| AA946876 | SOAT1 | DOWNSTREAM (3') OF SOAT1 |
| AK001844 | OLAH (THEDC1) | oleoyl-ACP hydrolase, thioesterase domain containing 1 |
| AI125696 | OLAH (THEDC1) | oleoyl-ACP hydrolase, thioesterase domain containing 1 |
| NM_018324 | OLAH (THEDC1) | oleoyl-ACP hydrolase, thioesterase domain containing 1 |

METHOD OF TREATING ACNE

This application is a continuation of U.S. Ser. No. 12/863,251, filed Jul. 16, 2010, which is a §371 national stage of PCT International Application No. PCT/IB2009/050271, filed Jan. 23, 2009, claiming priority of European Patent Application No. 08150554.7, filed Jan. 23, 2008, the contents each of which are hereby incorporated by reference in their entirety into this application.

The present invention relates to a composition for topical use, intended for the treatment and/or prevention of skin function dysfunctions. The present invention relates more specifically to a pharmaceutical composition for topical use, intended for the treatment and/or prevention of dysfunctions of sebaceous function, of healing, of atrophy termed "dermatoporosis (Ref Dermatology 2007.215. 284-294)", of estrogen deprivation of skin and of defense against infection.

Treatments already exist for the dysfunctions mentioned above, but they are not, however, without faults. Thus, by way of examples:
  it is known that a vitamin A derivative, isotretinoin (or 13-cis retinoic acid), is active in the treatment of diseases such as hyperseborrhoea and acne by inducing atrophy of the sebaceous glands. However, this substance must be administered systemically and not topically, since, when administered topically, it does not atrophy the sebaceous gland.
  In order to facilitate the healing of skin wounds, it is known practice to protect the tissues undergoing reconstruction, in particular by means of hydrocolloid dressings, but this technique provides superficial mechanical protection without specifically stimulating the intrinsic processes of tissue repair per se, when a deficiency exists in the production of growth factors, in particular vascular growth factors.
  It has been proposed to treat dermatoporosis by means of retinoids and of hyaluronic acid fragments, but the first can be irritant and the second can be difficult to prepare in their optimal size and viscosity.
  In the case of estrogen deprivation of the skin, which contributes to the skin becoming fragile and to dermatoporosis, it is known practice to administer estrogens systemically or topically. However, this supply of exogenous hormones has the drawback of modifying, as a whole, the patient's hormone balance and, according to several publications, of increasing the risk of appearance of certain cancers.
  In order to reinforce the capacities for defense against infection in the event of exposure or of susceptibility to bacterial skin infections, long-term antibiotic use has already been proposed, but this method has the fault of selecting resistant strains and of not increasing the intrinsic defenses of the individual.

There remains, therefore, an unmet need to develop new medicaments against the dysfunctions mentioned above, and in particular pharmaceutical compositions for topical use which make it possible to avoid the drawbacks associated with systemic administration.

Compounds which interact with the AhR receptor (aryl hydrocarbon receptor), the prototype of which is 2,3,7,8-tetrachlorodibenzo-p-dioxin (TCDD) are mostly xenotoxic compounds, inducing various types of tissue lesions and other manifestations of poisoning, which are dose- and species-dependent. The skin holds a major place among these manifestations of dioxin poisoning, partly due to the acknowledged expression of the AhR receptor by the epithelial and mesenchymal cells of the skin. For this reason, the therapeutic and/or preventive use of such compounds as active agents that modulate skin functions appears, in principle, to be excluded.

During human poisoning with TCDD, a complex syndrome is observed at the level of the skin. The detailed study of this syndrome in humans and in experimental animals has led the applicant to observe the cellular and molecular mechanisms that form these toxic lesions. Surprisingly, the applicant has discovered certain favorable effects of exposure to these toxic compounds, described below, and has found means for obtaining them, in the absence of the toxic effects mentioned above, for modulating skin functions, in particular sebaceous function, defense against infection, healing, skin atrophy termed "dermatoporosis (Ref. Dermatology 2007.215. 284-294)", and estrogen deprivation.

Consequently, the invention relates to compounds which are agonists of the AhR receptor and/or the proteins involved in its cellular activation pathways, these compounds acting in the context of the invention as agents for modulating skin functions, in particular sebaceous function, defense against infection, healing, atrophy termed "dermatoporosis", and estrogen deprivation of the skin.

According to a first aspect of the invention, the subject of said invention is a pharmaceutical composition for topical use, intended for transiently inducing the activation of AhR receptors of skin tissues, said composition comprising an active substance chosen from metabolizable agonist ligands of AhR, and from the in situ precursors of said ligands.

The toxicity of xenotoxic AhR ligands, such as TODD, appears to be essentially due to the fact that these substances are stored by the human organism, in the tissues of which they exhibit sustained half-lives, sometimes of the order of 4-12 years. As a result, the TCDD molecules continually released from the storage sites such as the fat tissue, to the target tissues expressing the AhR receptor, such as the skin, continuously activate the AhR signaling pathway, thereby leading to pathological effects. Thus, unlike with TCDD, through the use of defined metabolizable AhR ligands, the half-life of which in the organism can be evaluated in hours or in days, the topical activation of skin AhRs results only in a beneficial activation of certain skin functions, TCDD poisoning having made it possible to identify these functions for the first time in humans.

In this perspective, the active substance can be chosen from endogenous AhR ligands: the applicant considers that there are very probably endogenous ligands, or exogenous, in particular environmental, ligands, which give the AhR signaling pathway a physiological function. These ligands essentially have a short lifetime.

Thus, according to a $2^{nd}$ aspect of the invention, the subject of said invention is a composition for topical use, intended for transiently inducing the activation of AhR receptors of skin tissues, said composition comprising an active substance chosen from AhR agonist ligands with a short half-life and the in situ precursors of said ligands.

The ligands used in the context of the present invention preferably have half-life times in the human organism of between 2 and 96 hours, and more specifically, and according to the application, between 6 and 24 hours.

The present invention is therefore completely distinct from, and even antinomic to, certain prior art inventions which have proposed the use of AhR receptor antagonist ligands, with a view to preventing gene expression of the type of those that can be induced by exposure to TCDD and other xenotoxic AhR ligands. These inventions, described in particular in documents WO2004/041758, WO2007/060256 and WO2007/128725, were based on extrapolations drawn from in vitro experiments and on the premise that activation of the AhR pathway would by definition be harmful. On the contrary, the applicant has noted that the activation, in humans and experimental animals, of the AhR pathway can have favorable effects for the treatment of diseases such as abnormalities of sebaceous function, of healing, of atrophy termed "dermatoporosis", of defense against infection and of estrogen deprivation of the skin.

The ligands according to the invention are chosen such that they preferably meet four criteria:
1. An ability to activate the AhR receptor.
2. An ability to modulate a specific gene regulated by AhR.
3. A short half-life in the human organism, preferably of between 2 hours and 96 h, and more specifically, and according to the application, between 6 and 21 hours.
4. Preferably, a measurable positive effect on a recognized criterion of sebaceous hyperactivity, of wound healing, of dermatoporosis, of bacterial colonization of the skin, and/or of estrogen deprivation.

The modulated gene may in particular be the CYP1A1 gene. This modulated gene may also be one of the numerous genes described in the present application as being modulated by exposure to TCDD and the promoter of which expresses an AhR-binding site. The applicant considers that the modulation of the CYP1A1 gene is proposed as a paradigm based on current observations and knowledge; thus, it does not exclude the desired effects being obtained by means of AhR ligands which do not have activation of CYP1A1 expression as their predominant effect. The applicant considers, furthermore, that the lifetime should be a determining element in the beneficial effects/toxic effects dissociation by inducing a transient activation of AhR. However, the applicant does not exclude the possibility that certain ligands, the half-life of which departs from the numerical values indicated above, having this property of beneficial effects/toxic effects dissociation. This is because the duration of activation of the AhR receptor in the skin might not depend exclusively on the half-life of the ligand in the organism.

In general, the dissociation between beneficial effect according to the invention and toxic effects is obtained by stimulating the AhR receptor in a modulated and transient manner, i.e. in a manner close to the physiological action of the nontoxic, natural endogenous/exogenous ligands. This dissociation can also be obtained by the formation of a ligand, in situ, from a topically administered precursor. Said active substance can be a precursor chosen from the metabolic pro-ligands of AhR ligands. Said active substance may also be a precursor that can be activated so as to give an AhR ligand under the effect either of a physical agent, in particular under the effect of UV radiation, or of any other biological process, such as metabolic activation within a skin tissue by the saprophytic or pathogenic flora.

The invention will be understood more clearly by those skilled in the art through the description hereinafter of several specific applications, with reference to the corresponding examples and to the accompanying figures, in which:

FIG. 2 shows the disappearance of the sebaceous glands of the ear skin of C57BL/6 mice treated once a day for 45 d with 2 mcg/ml TCDD (bottom photograph) compared with the control (top photograph).

FIG. 3 shows the reduction in the surface area of the sebaceous glands in the ears of C57GL/6 mice treated once a day for 45 d with various ligands according to the invention.

Figure 4A:
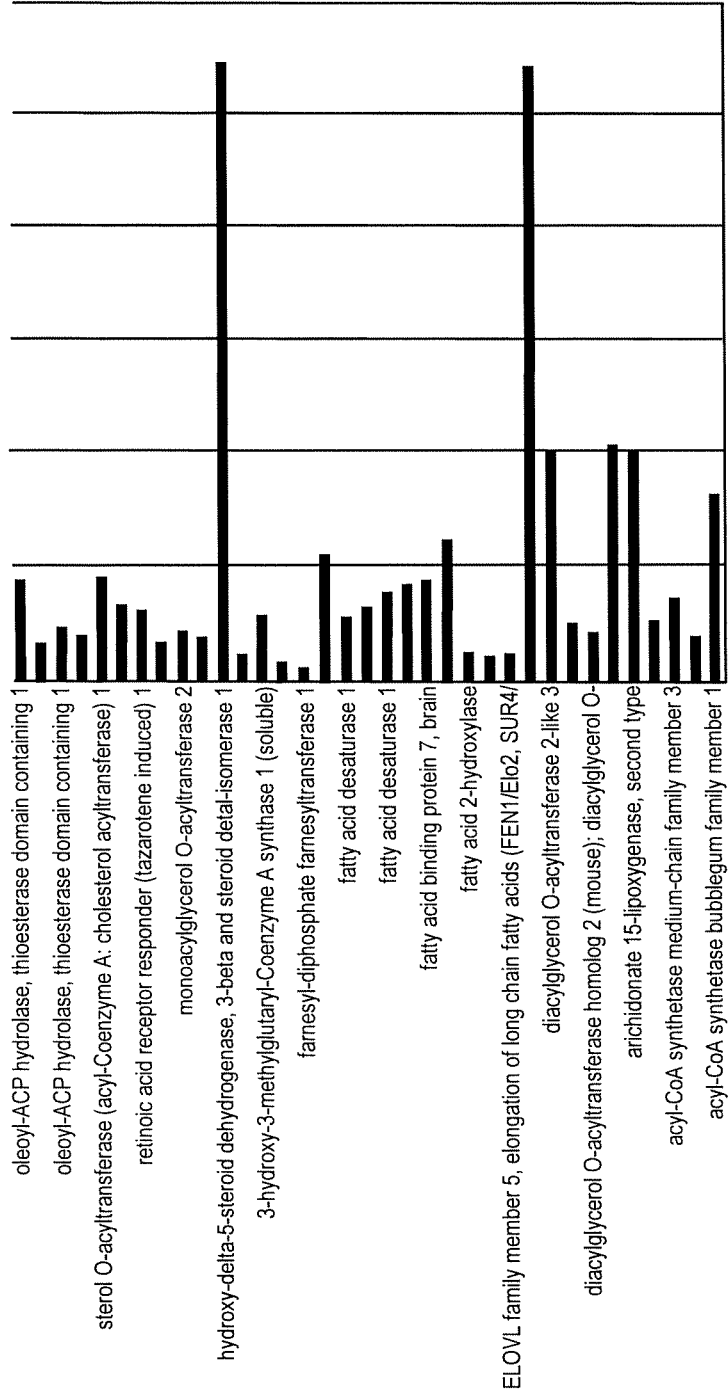

FIG. 4A shows the major inhibition of the gene expression of key enzymes of sebaceous lipogenesis in humans exposed to TODD, by analysis of the whole transcriptome (Affymetrix) in human skin exposed to TCDD: lipo/sebogenesis enzyme genes are greatly underexpressed. FIG. 4B and FIG. 4C show the symbols of the genes of which the expression is strongly repressed compared with the controls in human skin exposed to TCDD.

Figure 5:
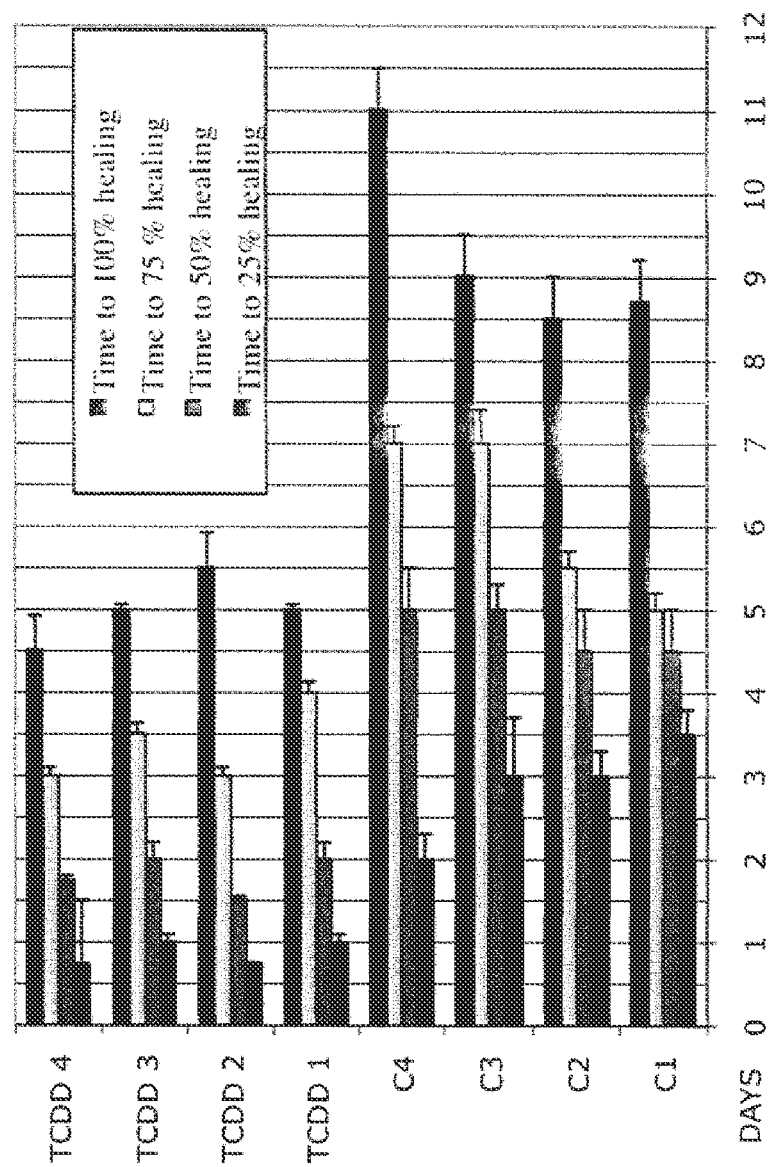
Figure 6:
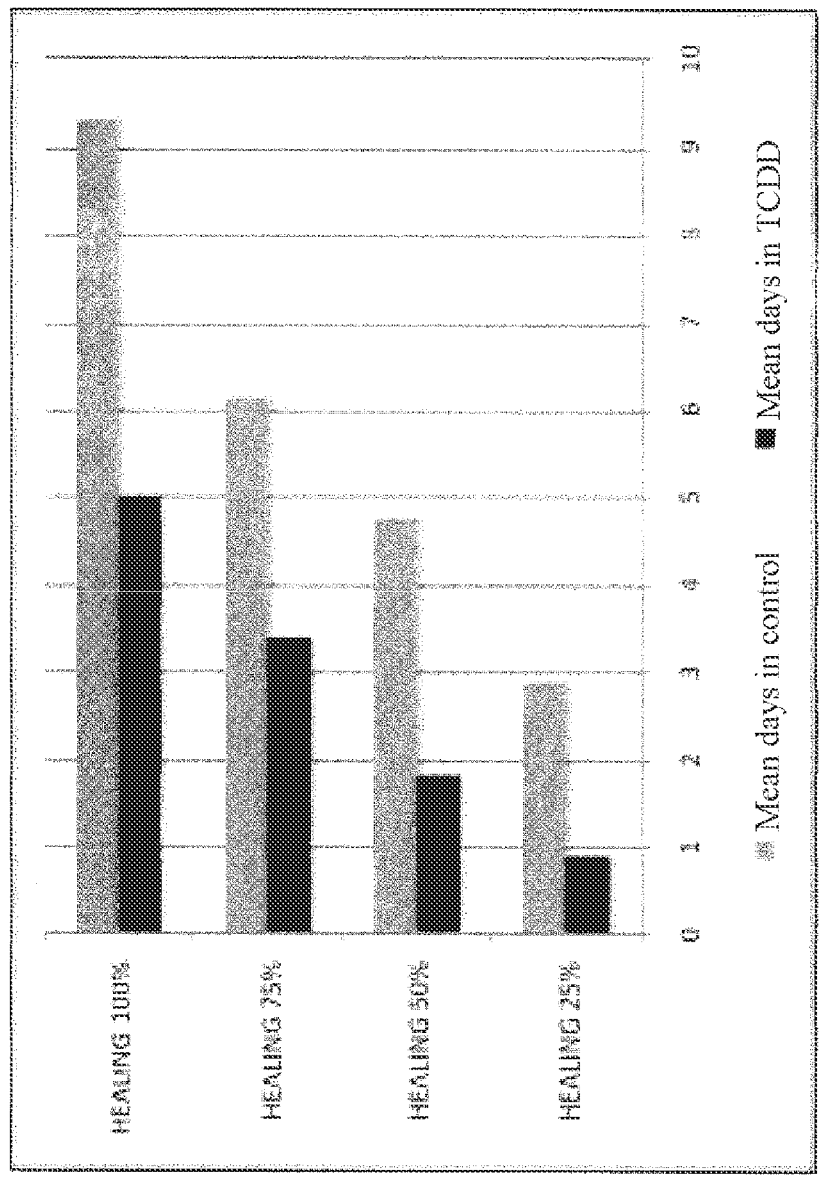

FIGS. 5 and 6 show the healing times of superficial wounds in the absence or in the case of exposure to TCDD in humans. FIG. 5 shows the percentage surface area healed as a function of time of 4 dermabrasions in the case of the presence of TCDD in the skin, in comparison with 4 controls (C1-C4).

FIG. 6 shows the mean values calculated on the basis of the data of FIG. 5. Thus, the time to complete healing is brought back from 9.3 (gray bars) to 5 days (black bars).

Figure 7:
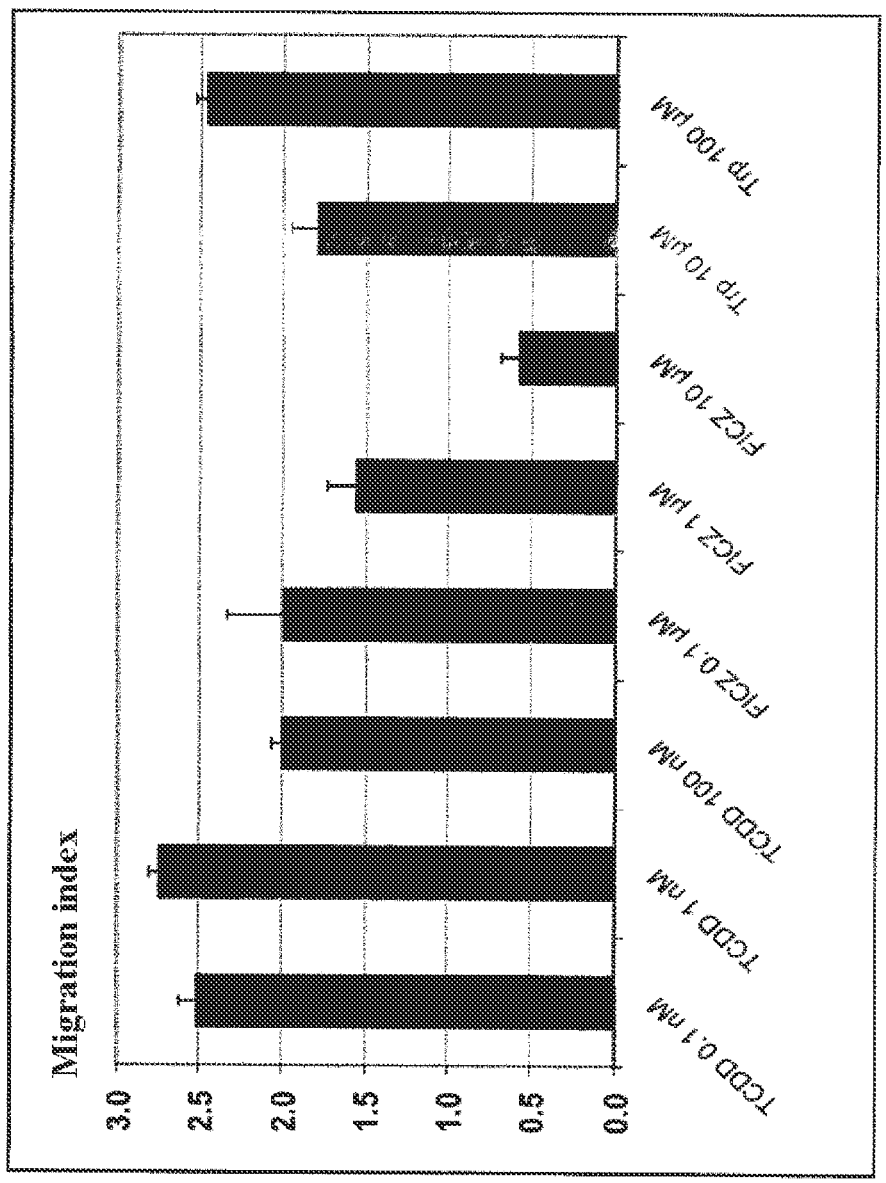

FIG. 7 shows the healing times of experimental wounds in a culture of human keratinocytes in vitro, treated with TCDD and with ligands according to the invention.

Figure 8:
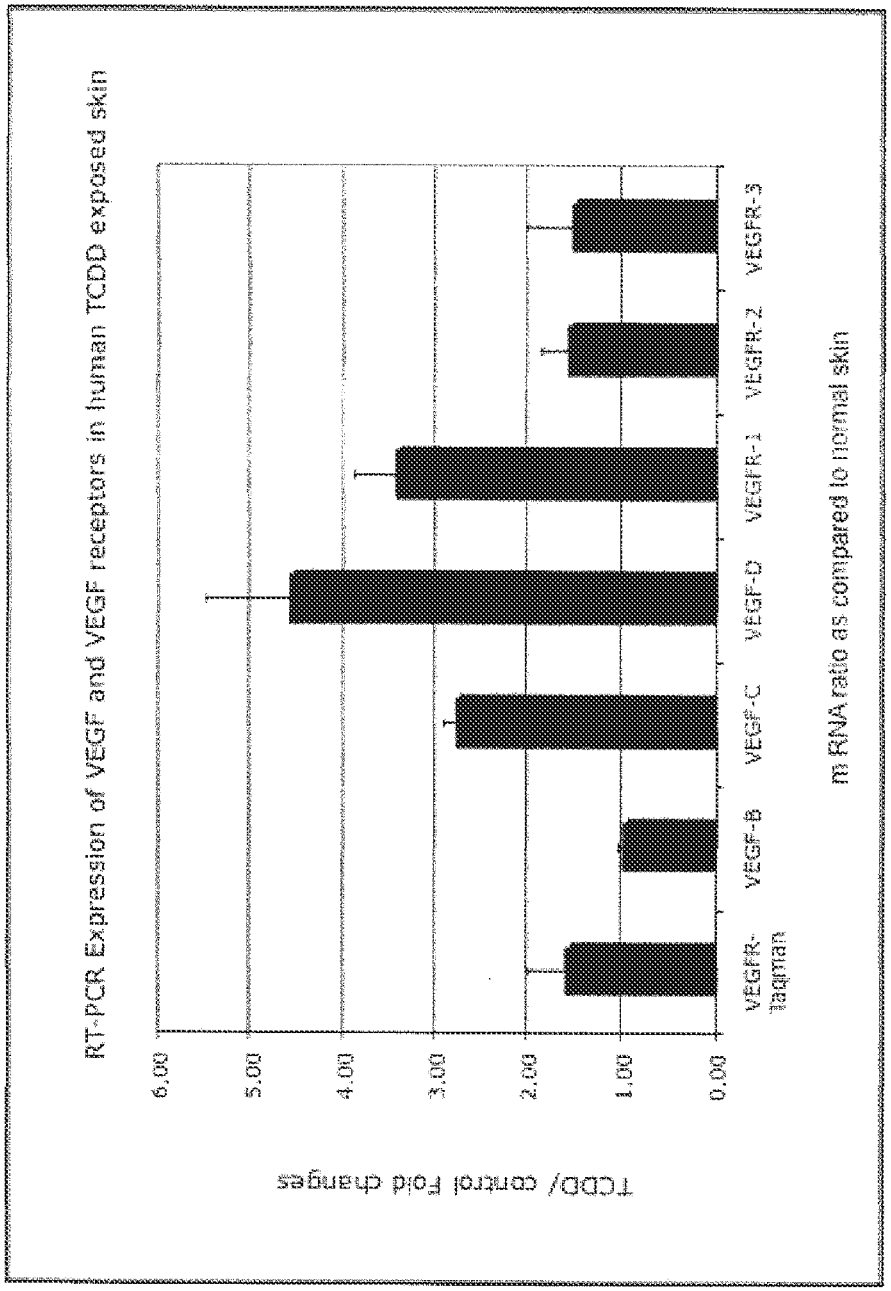

FIG. 8 shows the expression of the messenger RNAs of growth factors and of their receptors in human skin exposed to TCDD in vivo.

Figure 9:
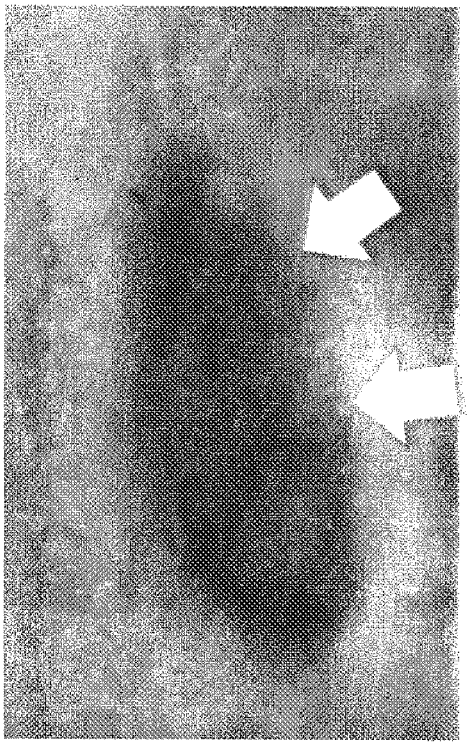
Figure 9:

FIG. 9 shows the healing of a chronic human wound to which a solution of Trp generating AhR activation according to the invention has been applied for 10 days. Contraction of the chronic wound is noted; the arrows show the development of epithelial healing with strips of keratinocytes migrating from the edges.

Figure 10:
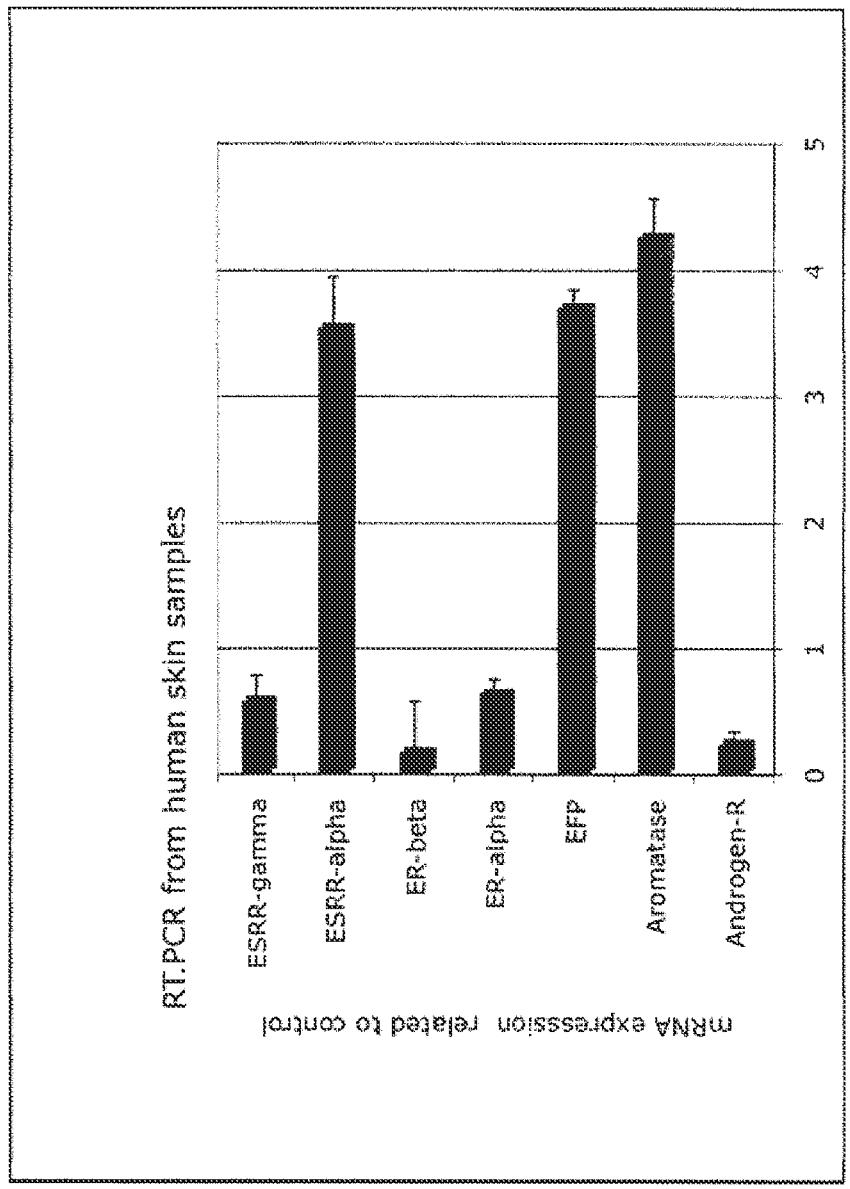

FIG. 10$a$ shows the induction, in the skin, of messenger RNAs of estrogen receptors and of aromatase by exposure to TCDD in a man.

FIG. 10$b$ shows the strong ectopic and focal expression of the ER-alpha receptor protein in the pilosebaceous structures on a specimen of the skin of an individual exposed to TCDD.

Figure 11:
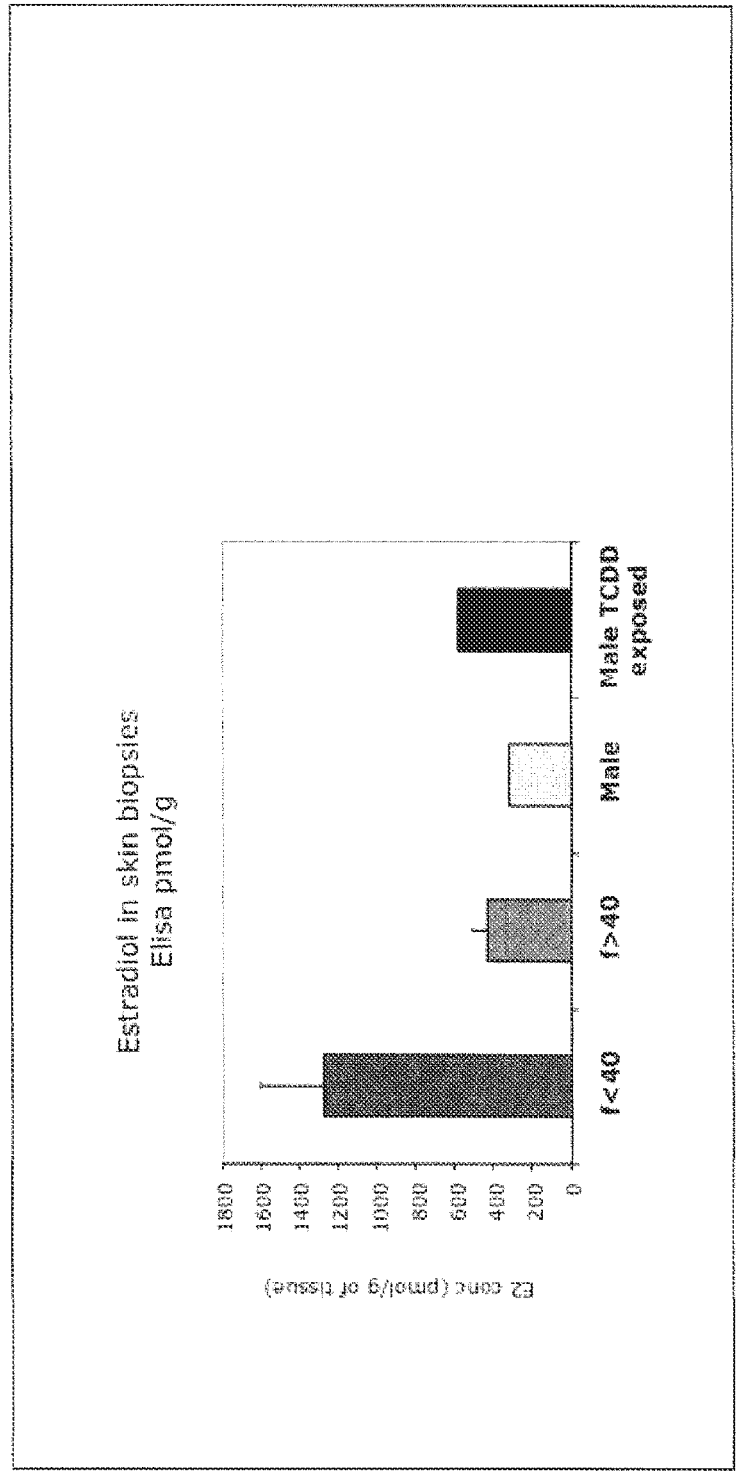

FIG. 11 shows the concentration of estradiol (E2) in human skin exposed to TCDD, determined by ELISA on fragments of human skin.

Figure 12:
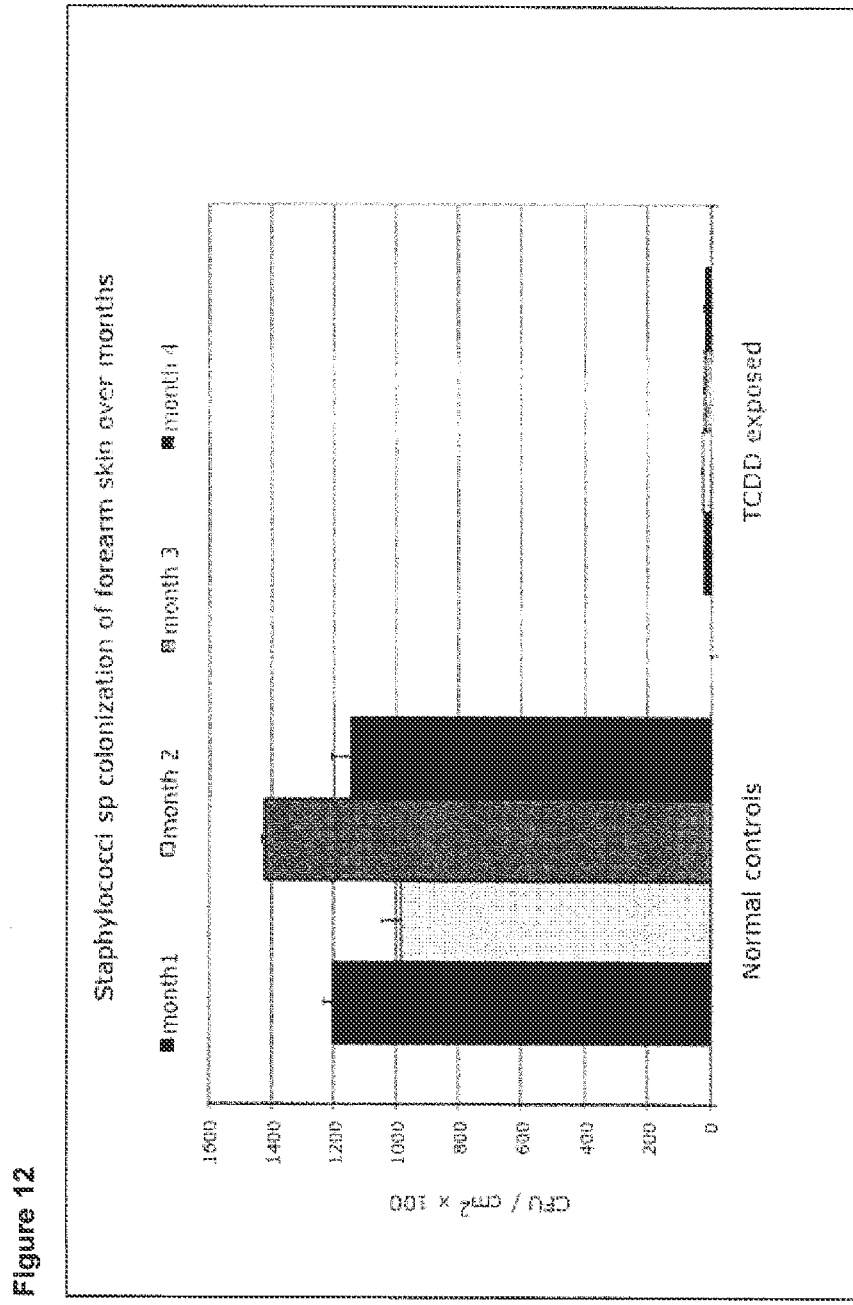

FIG. 12 shows the decrease in *staphylococcus* sp. colonization of human skin exposed to TCDD (data over four months).

Figure 13:
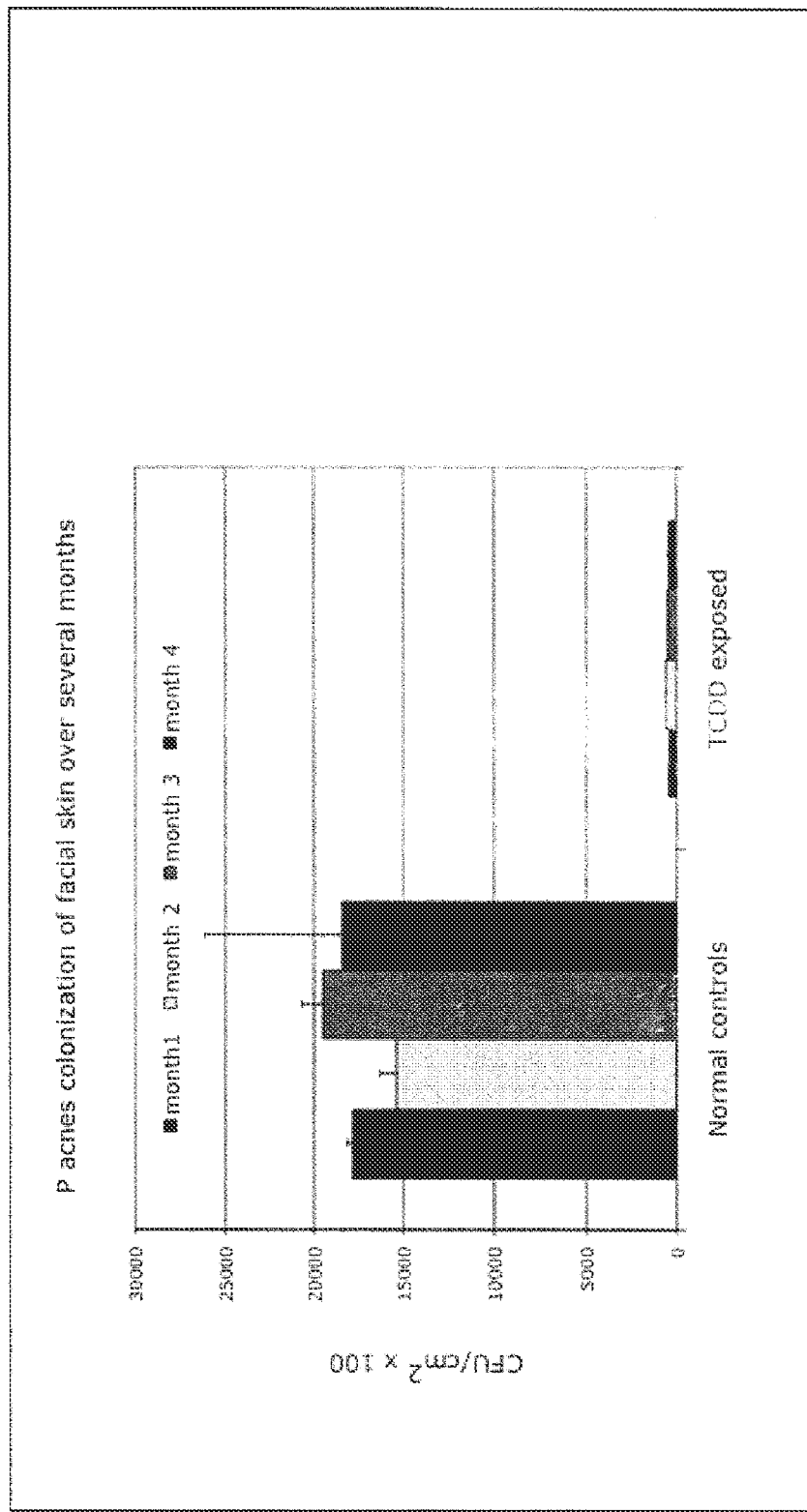

FIG. 13 shows the decrease in the colonization of human facial skin by *Propionibacterium acnes*, in skin exposed to TCDD (data over four months).

Figure 14:
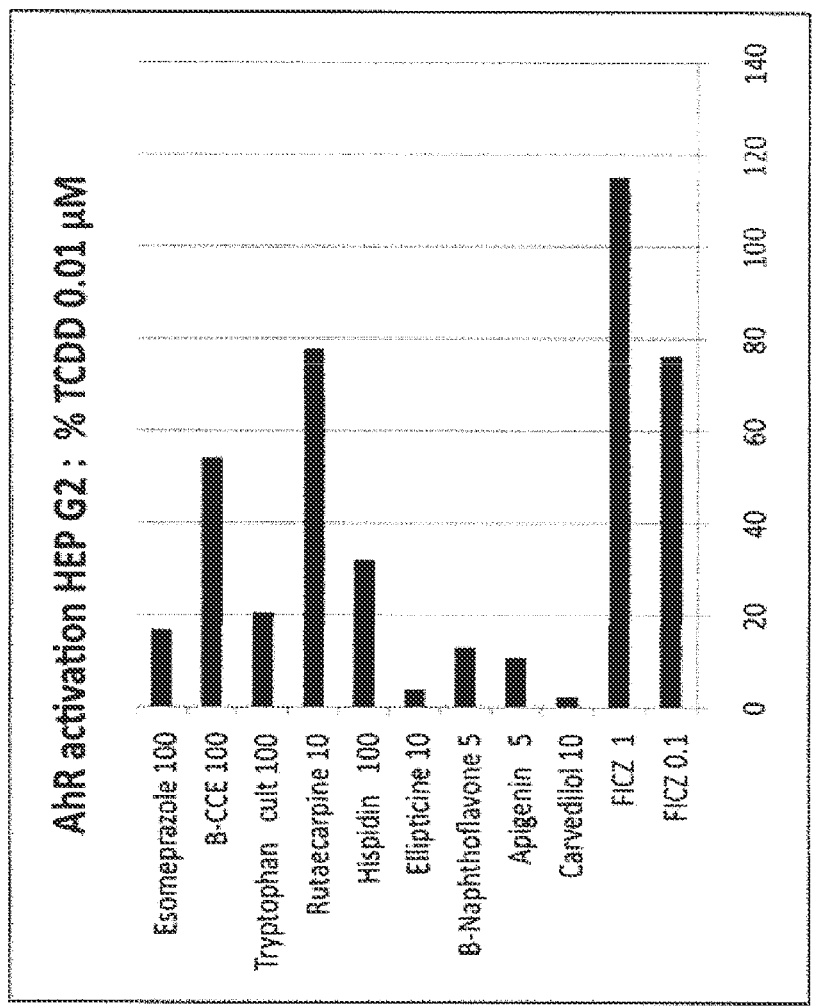
Figure 15:
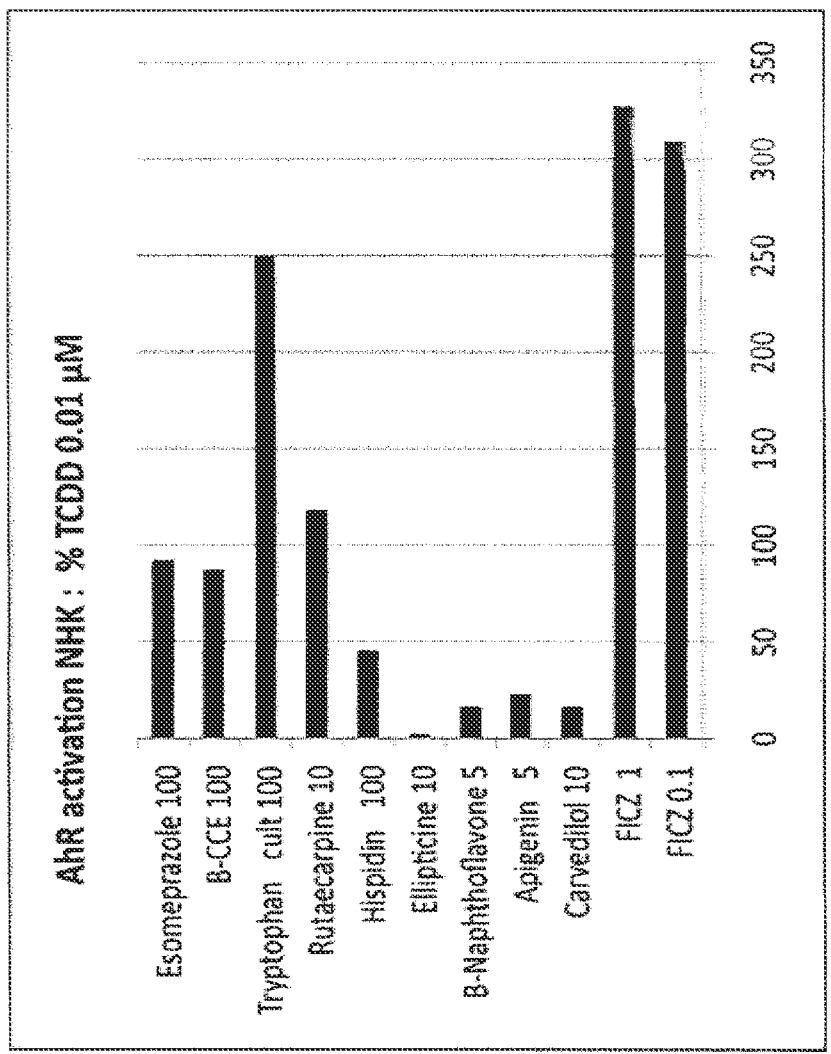

FIGS. 14 and 15 show the AhR receptor activation values in two cell types using various products with the aim of identifying active substances which activate AhR but the half-life of which is short. FIG. 14 shows the AhR activation of HEP G2 cells by various ligands according to the invention. The values represent the percentage activation compared with that obtained with 0.01 μM TCDD, using the concentration, in μM, most active in the range tested for each substance. FIG. 15 shows the AhR activation of keratinocytes by various ligands according to the invention. The values represent the percentage activation compared with that obtained with 0.01 μM TCDD, using the concentration, in μM, most active in the range tested for each substance.

Figure 16:
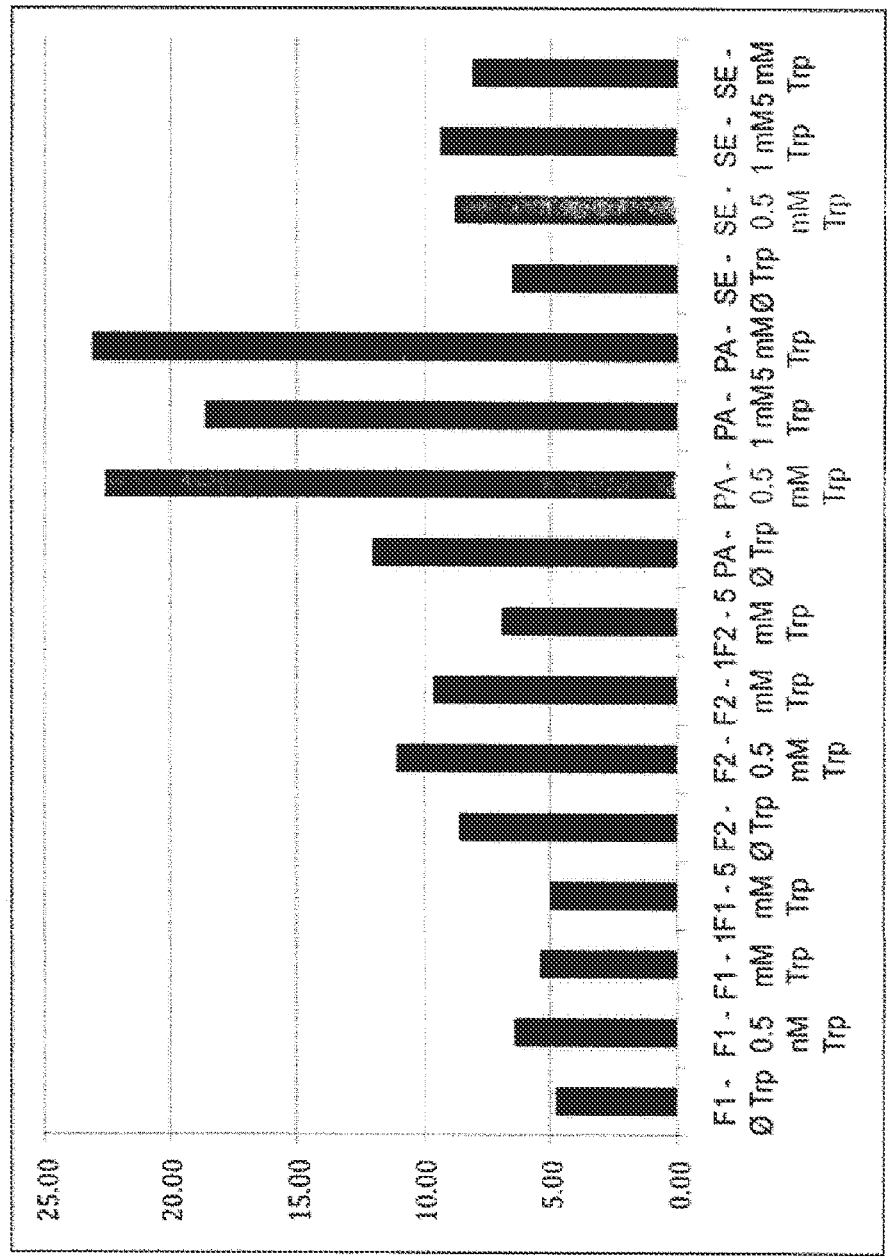

FIG. 16 shows the activation of AhR by various extracts of common human skin bacteria in the presence of tryptophan.

Figure 17:
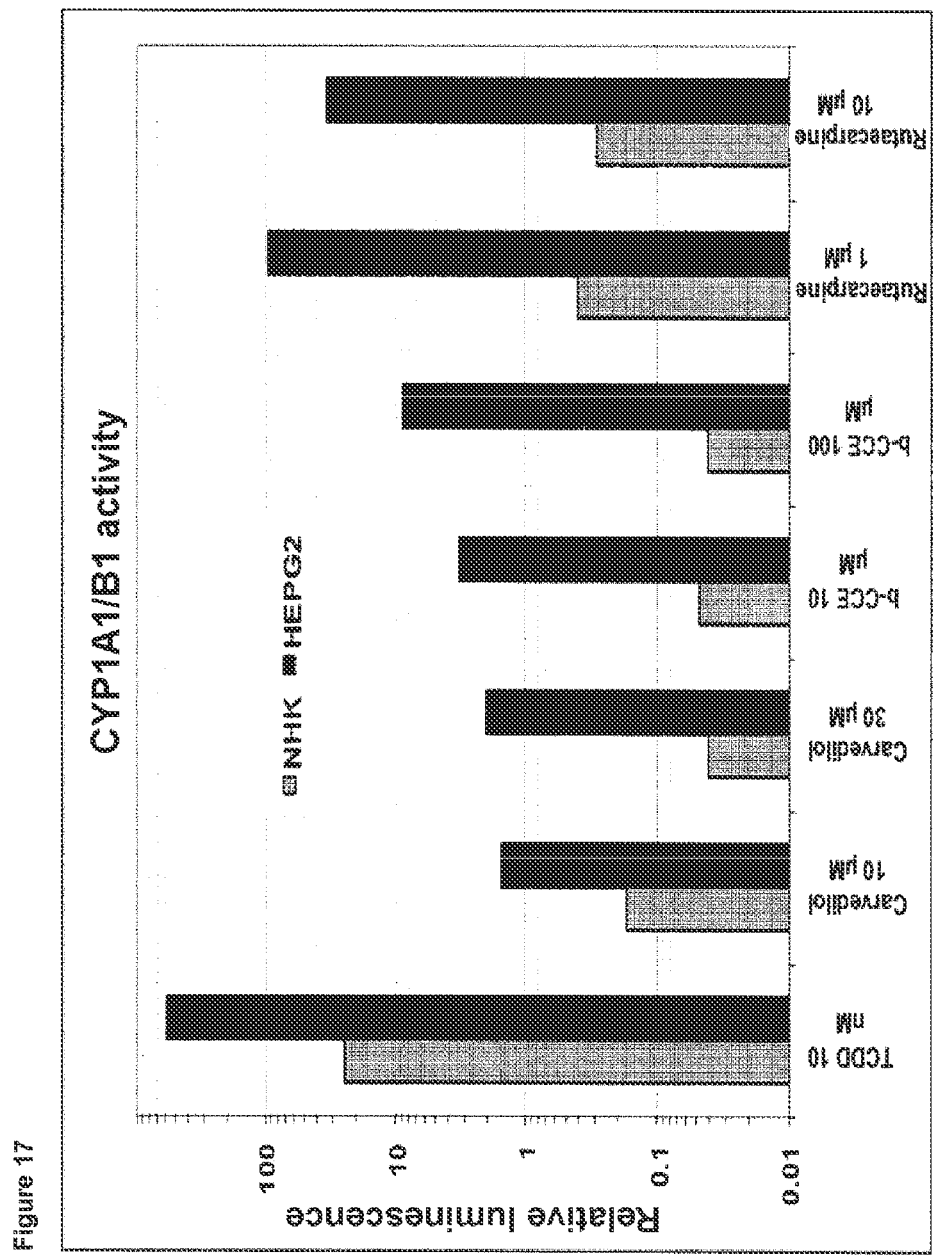

FIG. 17 shows the induction of a specific biological activity, CYP1A1, by AhR-activating ligands according to the invention. The tests are carried out using the "P450-GLO assay" kit from Promega.

As regards the sebaceous glands, the useful effect of TCDD, for the purpose of the present invention, is the gradual decrease in the size of the glands, and also the decrease in the expression of the genes of key enzymes in sebaceous lipogenesis.

Figure 1:
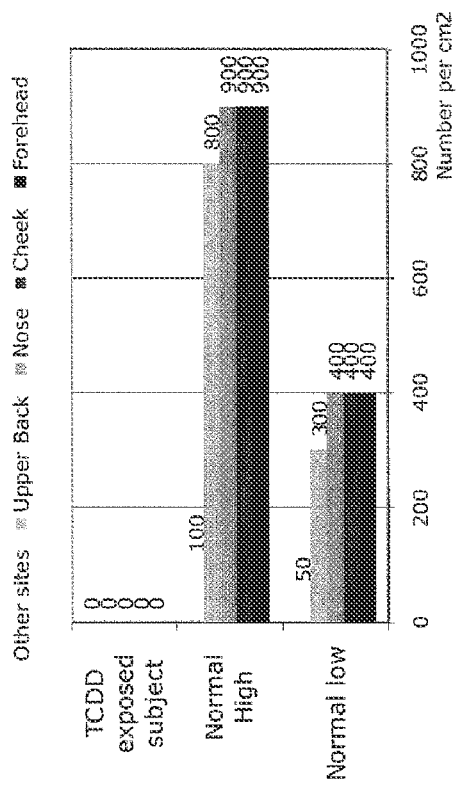
FIG. 1 shows the disappearance of sebaceous glands owing to exposure to orally administered toxic doses of TCDD in humans.

This decrease is observed in humans, from a morphological (histology) point of view, after a period of 2 to 4 weeks after exposure and becomes complete around week 8 (FIG. 1). The comparative data concerning normal human skin, presented in FIG. 1, were published by Montagna (1963).

Strong and focal expression of the CYP1A1 enzyme (mRNA and immunohistochemistry) is observed at the level of the sebaceous glands, and then in the hamartomatous metaplasia thereof in MADISH. This indicates a strong AhR-dependent activation at the level of the sebaceous glands and demonstrates, for the first time, that this organ is an AhR-dependent target, which can therefore be modulated by agonists of this receptor. This effect is not observed on the other skin structures (hairs, sweat glands, differentiation of the epidermis), which has led the applicant to consider that the effect on the sebaceous gland results from an inhibition of the differentiation of the sebaceous stem cell via the TCDD/AhR pathway. Thus, our analysis of the transcriptome of human skin exposed to TCDD indicates that the molecular target downstream of the TCDD/AhR pathway might be the human analog of blimt (a murine transcription factor which ensures the promotion of the sebaceous stem cell (Cell 126, 597-609, 2006)).

This thus results in a very considerable decrease in the enzymes of sebaceous lipogenesis, as attested to by the analysis of the transcriptome of human skin exposed to TCDD (FIG. 4).

Figure 10B:
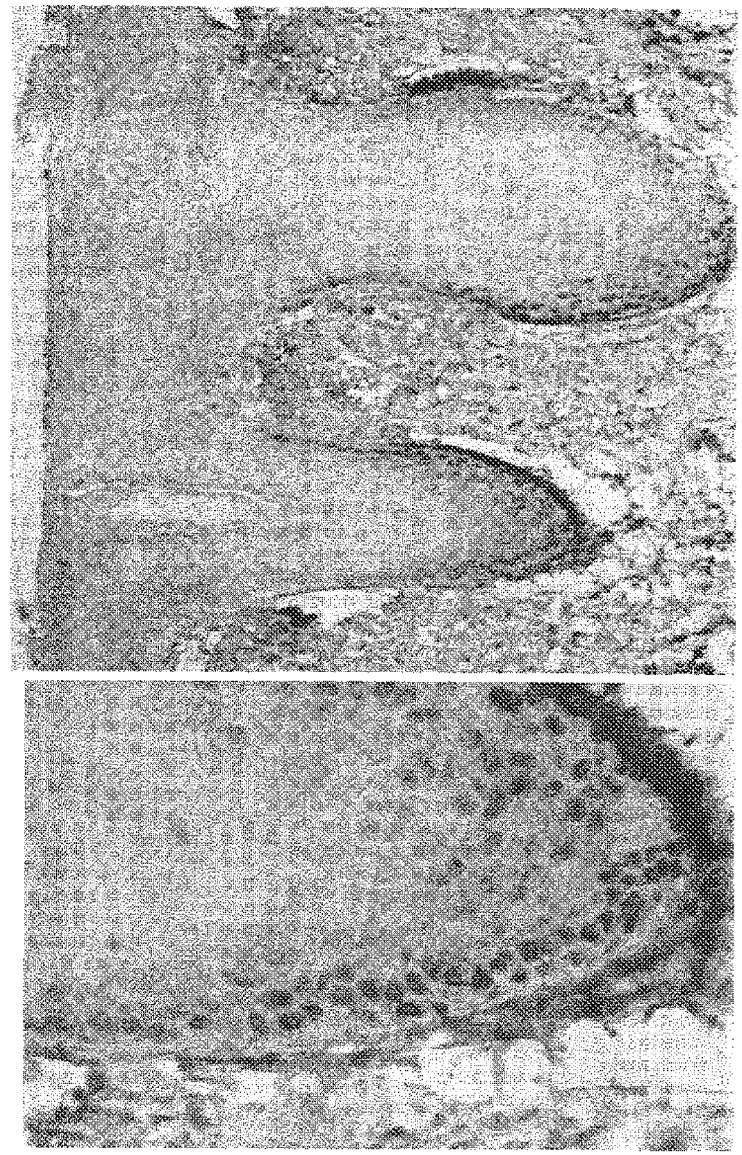

It should also be emphasized that the TCDD-exposed human skin immunohistochemistry reveals strong and focal expression of estrogen receptors at the level of the sebaceous glands (FIG. 10b).

These data have led the applicant to design a new approach for modulating sebaceous hypertrophy. This approach comprises the activation of AhR-dependent pathways in the sebaceous glands by means of agonists of this receptor. It involves the inhibition of sebaceous stem cell differentiation factors and of sebocyte proliferation, the inhibition of sebaceous lipogenesis enzymes, and also the local stimulation of estrogen production pathways and the local overexpression of estrogen receptors.

This effect of gradual decrease in the size of the sebaceous glands can be reproduced in animals by topical application of TCDD. This effect is specific since, in humans, there is no atrophy of the other secondary structures such as hairs and sweat glands. Thus, the present invention uses the effect of specific inhibition of the sebaceous gland by means of an AhR ligand for the prevention and treatment of diseases comprising a hypertrophy of these glands, such as hyperseborrhoea and acne, by inducing sebaceous gland atrophy. For this application, this invention offers a spectrum of activity that is potentially identical to that of oral isotretinoin, but via topical administration. The invention also identifies the key enzymes of sebaceous lipogenesis and also the factors which ensure promotion of the sebaceous stem cell as a target for AhR activators, but also potentially other chemical modulators that may have a therapeutic application. A therapeutic application against sebaceous gland tumors and analogs thereof, such as carcinomas with sebaceous differentiation in Muir-Torre syndrome, is also envisioned.

The AhR ligands used to reproduce this effect are chosen on the basis of a reduction of at least 40% in the size and number of sebaceous glands, without the induction of toxic signs, and also a reduction in the expression of the key enzymes of sebaceous lipogenesis. The means for obtaining the effect on sebaceous glands without inducing other toxic effects of the TCDD type, particularly the formation of hamartomatous structures (Metabolizing Acquired Dioxin Induced Skin Hamartomas, MADISH), comprise the use of compounds that transiently interact with the AhR receptor, such that the kinetics are favorable to this temporal dissociation between favorable effect and toxic effects.

As regards healing and atrophy of the skin termed "dermatoporosis (Ref. Dermatology 207.215. 284-294)", the useful effect of TCDD noted by the applicant manifests itself through impressively quick wound healing. Thus, the applicant has observed that epidermal-dermal wounds, the average healing time of which is ordinarily 10 days, are covered in 3 days. This effect is in line with the induction by TCDD of several growth factors (Vascular Endothelial Growth Factor VEGF, amphiregulin, TGFb, PDGF, IGF, hepatocyte growth factor hepapoietin A; scatter factor) and of receptors thereof, and also of thrombospondin 1. These data have been obtained by analysis of the whole transcriptome (Affymetrix) in several samples of skin from a man exposed to TCDD, in comparison with human controls. The effect of TCDD is further characterized by a very substantial accumulation of hyaluronate in the dermis, in parallel with hyperexpression of hyaluronate synthases.

A subject of the invention is therefore a pharmaceutical composition that can be administered topically, intended for treating and preventing skin healing problems and delayed skin healing, in particular associated with dermatoporosis, this composition comprising at least one compound that interacts as an agonist with the AhR receptor. The means for obtaining the desired effect without inducing other toxic effects of the TCDD type comprise the use of compounds of which the kinetics of interaction with the AhR receptor are favorable to this dissociation: the invention in particular proposes in situ production from a precursor such as tryptophan (Trp) or a Trp derivative, administered in a pharmaceutical carrier, enabling transcutaneous bioavailability, followed by exposure to UV radiation, or else the application, in a chronic wound, of Trp in a suitable carrier, enabling the generation, in situ, by the medium, of AhR ligand according to the example shown in FIGS. 7, 9, 14-17, the interaction with the AhR receptor being limited by the metabolization in situ by phase 1 enzymes.

Another subject of the invention is therefore a pharmaceutical composition that can be administered topically, intended for treating and preventing skin atrophy termed dermatoporosis (Ref. Dermatology 2007.215. 284-294), which is characterized by a depletion of hyaluronate resulting in a loss of the viscoelasticity of the skin, this composition comprising at least one compound that interacts as an agonist with the AhR receptor, or a precursor of said compound, of the type described above.

As regards estrogen deprivation, the useful effect of TCDD manifests itself through an activation of the estrogen production pathways and also through an overexpression of estrogen receptors. Estrogens are endogenous hormones that are very important in many skin functions: estrogen deprivation leads to problems with each of these functions. It is in particular a factor involved in dermatoporosis. It is moreover known that the Local administration of estrogens is a conventional means, which is nevertheless not without risk, for combating hyperseborrhoeic conditions and androgenetic alopecia. Exposure to TCDD leads, in the skin, to a strong expression of the genes for estrogen receptors and for the aromatase enzyme (FIG. 10), and also an increase in cutaneous estradiol (FIG. 11). The immunohistochemistry of these specimens reveals a strong and very focal expression of the receptors at the level of the pilosebaceous structures. Thus, the applicant has identified for the first time the local induction, by TCDD, of a state of hyperestrogenism focused on a skin structure which is known to be hormone-dependent. It is highly probable that this contributes to the decrease in the size of the sebaceous glands.

A subject of the invention is therefore a pharmaceutical composition that can be administered topically, intended for treating and preventing skin function problems associated with estrogen deprivation, this composition comprising at least one compound that interacts as an agonist with the AhR receptor. The means for obtaining the desired effect on estrogen expression without inducing other toxic effects of the TCDD type comprise the use of compounds of which the kinetics of interaction with the AhR receptor are favorable to this dissociation: the invention in particular proposes in situ production from a precursor such as tryptophan or a Trp derivative, administered in a pharmaceutical carrier enabling transcutaneous penetration, followed by exposure to UV radiation, the interaction with the AhR receptor being limited by the metabolization in situ by phase 1 enzymes.

As regards the defense against infection, the useful effect of TCDD noted by the applicant manifests itself through a marked resistance to skin infections. This resistance coincides with a continual stabilization of the surface flora to the benefit of nonpathogenic saprophytic species. This resistance results in an absence of superinfection by pathogenic microorganisms. It is in parallel with and probably partly associated with an overexpression of defensins, including beta-defensin. It is also in parallel with and no doubt at least partly associated with an overexpression of filaggrin. The two observations that have a therapeutic implication are, on the one hand, the reduction in staphylococcal colonization and, on the other hand, the reduction in colonization by *P. acnes*.

A subject of the invention is therefore a pharmaceutical composition that can be administered topically, intended for treating and preventing the effects of bacterial skin infections, in particular in individuals with a high susceptibility, and also other situations involving chronic carriers, this composition comprising at least one compound that interacts as an agonist with the AhR receptor. The means for obtaining the desired effect on skin infections without inducing other toxic effects of the TODD type comprise the use of compounds in which the kinetics of interaction with the AhR receptor are favorable to this dissociation: the invention in particular proposes in situ production from a precursor such as tryptophan or a Trp derivative, administered in a pharmaceutical carrier enabling transcutaneous penetration, followed by exposure to UV radiation, or else the generation, in situ, by the medium, of AhR ligand according to the example shown in FIGS. 7, 9, 14-17. It will in particular be noted that certain saprophytic and pathogenic strains of the skin surface generate AhR activation which is potentiated by the presence of tryptophan (FIG. 16).

Among the compounds which bind to AhR and are capable of producing the effects according to the invention, mention may be made, by way of nonlimiting examples, of:

Flavonoids
Flavonols with alkyl, alkenyl, alkoxyl or carboxyl substituents in positions 4 to 6 and 3' to 5'.
Flavanones with alkyl, alkenyl, alkoxyl or carboxyl substituents in positions 5, 6 and 3' to 5'.
Flavones with alkyl, alkenyl, alkoxyl or carboxyl substituents in positions 3, 5, 6 and 3' to 5'.
Flavonols with alkyl, alkenyl, alkoxyl or carboxyl substituents in positions 5, 6 and 3' to 5'.
Isoflavones with alkyl, alkenyl, alkoxyl or carboxyl substituents in positions 5, 6 and 3' to 5'
Anthocyanidins with alkyl, alkenyl, alkoxyl or carboxyl substituents in positions 4 to 6 and 3'
Epigallocatechin gallate; esterification in one or other of positions 5, 7, 3' to 5', 3" to 5" with fatty acids or retinoic acid.

Stilbenes
cis-Stilbenes with hydroxyl, alkyl, alkenyl, alkoxyl or carboxyl substituents in positions 1 to 5 and 1' to 5'.
trans-Stilbenes with hydroxyl, alkyl, alkenyl, alkoxyl or carboxyl substituents in positions 1 to 5 and 1' to 5'.

Tryptophan derivatives
Indole-3-carbinol; alkyl, alkenyl, alkoxyl or carboxyl derivatives on the hydroxyl group.
Tryptamine.
Kynurenine and ester of the carboxylic group with retinol.
Indoleacetic acid and ester of the carboxylic group with retinol.
Indolepyruvic acid and ester of the carboxylic group with retinol.
6-Formylindolo[3,2-b]carbazole and alkyl or alkenyl derivatives of the formyl group.
3,3'-Diindolylmethane.
Trythanthrine.
Malassezin.
Indirubin.
Indigo.

Other ligands
ITE [methyl 2-(1'H-indole-3'-carbonyl)thiazole-4 -carboxylate] (endogenous, see US 20020183524).
YH439 {(isopropyl-2-(1,3-dithioethan-2-ylidene)-2 -[N-(4-methylthiazol-2-yl)carbamoyl]acetate}.
a-Naphthoflavone.
b-Naphthoflavone.
Hispidin.
Carvedilol.
Rutaecarpine.
Ethyl β-carboline-3-carboxylate.
Esomeprazole.
Fatty acid metabolites, in particular arachidonate metabolites.

The ligands are chosen in that they preferably meet four criteria:
1. An ability to activate the AhR receptor, as shown in FIGS. 14, 15 and 16 on two cell systems.
2. An ability to modulate a gene regulated by AhR, for example CYP1A1, which is shown in FIG. 17.
3. A short half-life in the human organism, preferably of between 2 hours and 96 h, and more specifically, and according to the application, between 6 and 24 hours.
4. A measurable positive effect on a recognized criterion of sebaceous hyperactivity, of wound healing and of dermatoporosis, of bacterial colonization of the skin, and/or of estrogen deprivation according to, but non exclusively, the examples given here for each of these effects.

Figure 3:
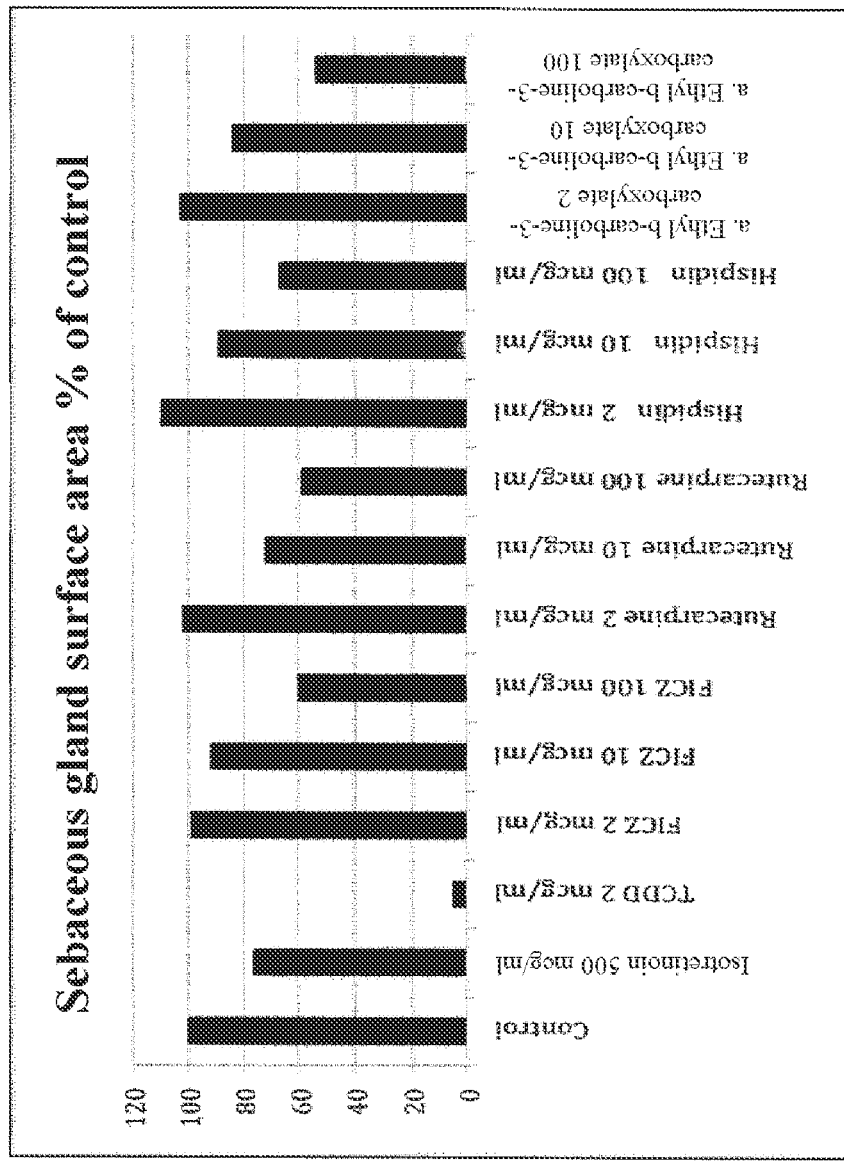
FIG. 3 illustrates the reduction in sebaceous glands through topical application of 4 ligands according to the invention.

Among the preferred AhR ligands, mention may be made of:
Flavonoids
a. Catechin
b. Apigenin
c. Epigallocatechin 3-gallate
d. Quercetin
e. Silibinin
Stilbenes and derivatives
f. Resveratrol
g. Yangonin Tryptophan and tryptophan derivatives
- h. Indole-3-carbinol
- i. Tryptamine
- j. Kynurenine
- k. 6-Formylindolo[3,2-b]carbazole (FICZ) illustrated in FIGS. 3, 14 and 15 and alkyl or alkenyl derivatives of the formyl group
- l. 3,3'-Diindolylmethane
- m. Trythanthrine
- n. Malassezin
- o. Indirubin
- p. Indigo Other ligands
- q. ITE [Methyl 2-(1'H-indole-3'-carbonyl)thiazole-4-carboxylate] (endogenous, see US 20020183524)
- r. YH439 {(Isopropyl-2-(1,3-dithioethan-2-yl-idene)-2-[N-(4-methylthiazol-2-yl)carbamoyl]acetate}
- s. Hispidin, illustrated in FIGS. 3, 14, 15
- t. alpha-Naphthoflavone
- u. beta-Naphthoflavone
- v. Ellipticine
- w. Carvedilol illustrated in FIGS. 14, 15, 17
- x. Triclabendazole
- y. Rutaecarpine illustrated in FIGS. 3, 14, 15, 16, 17
- z. Ethyl β-carboline-3-carboxylate (B-CCE) illustrated in FIGS. 3, 14, 15, 16, 17
- aa. Esomeprazole illustrated in FIGS. 14, 15.

The methods for delivering the AhR receptor ligand under the optimum conditions for the desired effect comprise:
- a. Direct application of the active ligand in a suitable galenic carrier such as a lotion, gel, cream, ointment, foam, impregnated dressing.
- b. Topical application, in a suitable galenic carrier, of a proligand, which will be metabolized to a ligand by the epidermal enzymes.
- c. Application of a proligand to the surface of the skin to be treated, which proligand will be activated to give a ligand by means of the effect of a physical agent such as UV radiation; for example, tryptophan and UVB or UVA, optionally in combination with riboflavin; or else, depending on the indication, by means of the endogenous or exogenous agents present in the disease treated: by way of example, activation of AhR ligand in the fluid of a chronic wound treated with tryptophan, or by *Propionibacterium acnes* on a seborrheic/acneic face treated with tryptophan (FIGS. 7, 9, 14, 15 and 16).

EXAMPLE 1

Sebaceous Glands

The sebaceous glands, which are present in large numbers in normal human skin, disappear during exposure to toxic doses of TCDD. FIG. 1 shows the number of sebaceous glands per square centimeter on various areas of the human body, which is distributed from 50 to 900 depending on areas and individuals. Thus, on the face of an adult, the number is between 400 and 900/cm².

FIG. 1 shows that, when there is exposure to TCDD, the sebaceous glands disappear in all the areas studied. For each site, 3 to 10 skin biopsies were analyzed after fixing with formol and staining with hematin-eosin. At least 10 sections per block were analyzed. Out of a total of 62 biopsies, totaling 620 sections, no sebaceous gland could be observed, whereas the number and structure of the sweat glands and the hairs were conserved. These data were obtained on specimens of human skin containing from 930 to 2900 ppt of TCDD measured by gas chromatography/mass spectrometry.

Figure 2:
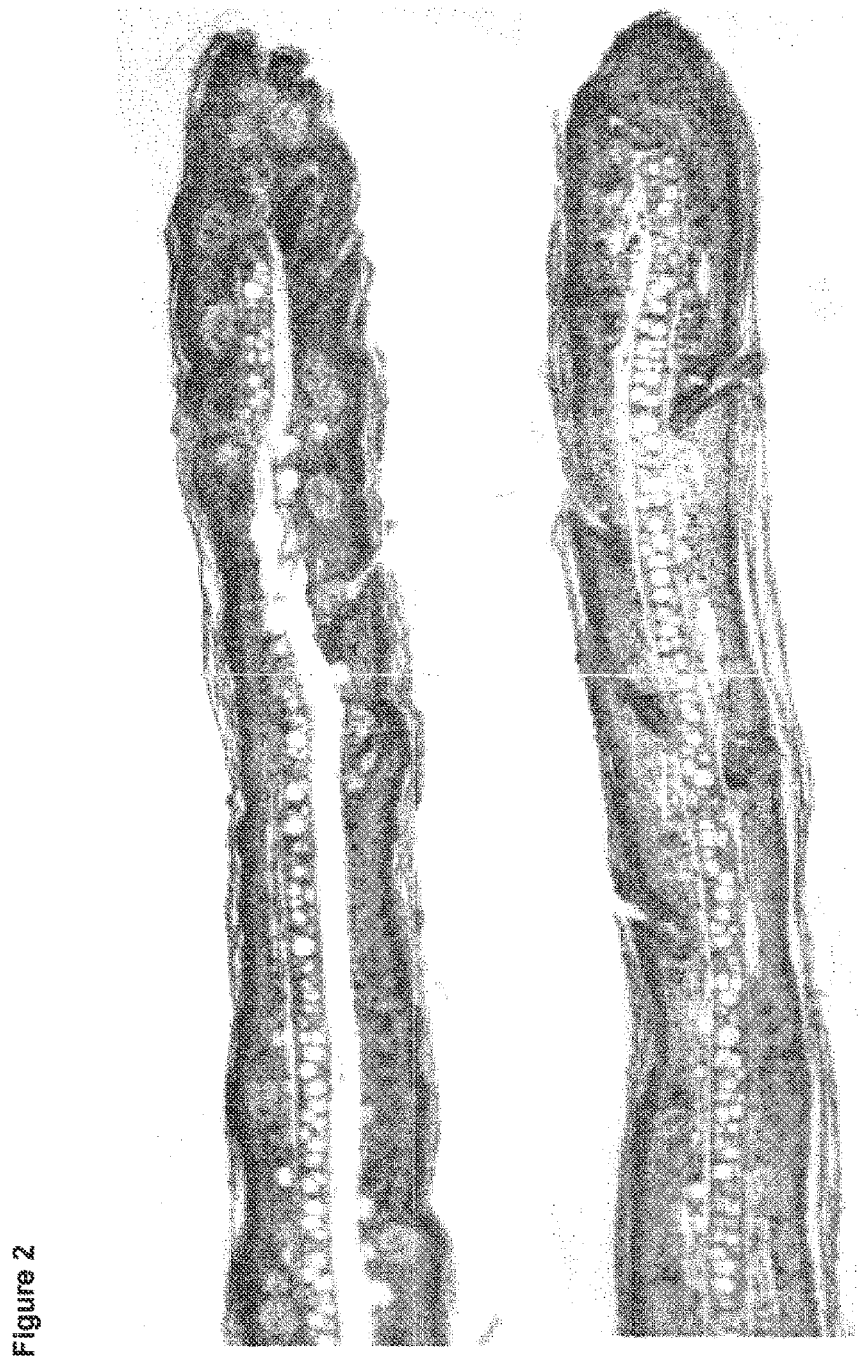
FIG. 2 illustrates the reproduction of this phenomenon of sebaceous gland disappearance by topical application of TCDD in mice.

The effect on the sebaceous glands can be reproduced in animals by topical application of TCDD. A 95% reduction in the number of sebaceous glands can be observed in 0570L/6 mice after 45 days of application of 2 mcg/ml TCDD (FIG. 2).

To reproduce the useful effect of TCDD, in a therapeutic reduction approach the reduction in the surface area of the sebaceous glands in the ears of C57BL/6 mice treated once a day for 45 d with various ligands according to the invention can be studied. The surface area of the sebaceous glands is measured on three serial sections per animal. A reduction of greater than 40% is sought, and obtained here with a concentration, a treatment time and an application frequency considered to be minimal. Isotretinoin is shown by way of example of a product used for the topical and systemic treatment of acne.

The topical application of an AhR ligand such as 6-formylindolo[3,2-b]carbazole (FICZ), at a concentration of 100 mcg/ml, makes it possible to obtain a significant decrease in the sebaceous glands, of the order of 40%. Other ligands according to the invention (see FIGS. 14, 15 and 17) also lead to a decrease in the surface area of the sebaceous glands. The data indicate that the optimum doses for a reduction of greater than 40% may be beyond the concentrations, the time and the application frequency shown in FIG. 3 and illustrate the concept of the invention.

FIG. 16 shows the activation of AhR of HEP G2 cells by various extracts of common human skin bacteria in the presence of tryptophan (trp) F1: G+flora; F2: G+flora; PA: *P. acnes*; SE: *S. epidermidis*. The activation value of 25.00 on the Y-axis corresponds to 1/6 of the AhR stimulation by 10 nM TCDD in this same system (157.00). It can be seen that, in particular with *P. acnes*, an increase in the activation is observed with the addition of tryptophan (trp). These observations illustrate the method of activation of AhR by tryptophan partly by interaction with the surface flora.

The effect shown in FIG. 16, where it is seen that *Propionibacterium acnes* (PA) generates an AhR activation, which is highly accentuated by the addition of tryptophan, can be taken advantage of in the context of this invention. This is because PA is one of the key players in sebaceous gland diseases, and it is present in large amounts in facial skin. It could therefore contribute to producing therapeutic amounts of AhR ligands in the presence of tryptophan, or also other aromatic amino acids such as tyrosine and phenylalanine. In order to explore the relevance of this approach, the applicant carried out a test by applying a gel containing 11 tryptophan to the face of two hyperseborrheic men for 3 weeks, and observed a decrease in the seborrhea which could be evaluated at 40% of the starting value using sebumetric measurement of the casual sebum levels.

FIG. 4A, FIG. 4B and FIG. 4C show the considerable reduction of messenger RNAs of several sebaceous lipogenesis enzymes in human skin exposed to TCDD. This observation identifies a new target for medicaments aimed at modulating sebaceous function, a concept exemplified here by AhR activation.

EXAMPLE 2

Healing and Skin Atrophy

The healing time of superficial epidermal-dermal wounds (dermabrasions) is considerably decreased by TCDD. FIG. 5 shows the percentage of surface area healed as a function of time of 4 dermabrasions in the case of the presence of TCDD in the skin (TCDD1-4, 930 to 2900 ppt TCDD measured by gas chromatography/mass spectrometry) in comparison with 4 controls (C1-C4). FIG. 6 shows the mean values calculated from the data of FIG. 5. Thus, the time to complete healing is reduced from 9.3 to 5 days.

FIG. 7 shows, in a model of wound healing in vitro on a culture of human keratinocytes, that the gap in the culture is repaired with TODD and with active substances according to the invention in proportions similar to what is observed after application of growth factors. The wound is induced by means of an incision with a yellow micropipette tip (10-200 µl). Migration index=value obtained with the ligand/that of the control without ligand. These results indicate a strong stimulation of healing with TCDD at nM concentrations, and with FICZ and tryptophan at µM concentrations. This indicates an activity of the AhR activation pathway on the migration of keratinocytes which is found in vivo in humans (FIGS. 5, 6, 10).

At the highest concentrations, a decrease in the effect, or even an inhibition of healing, is observed with TCDD and FICZ. Tryptophan (Trp) generates, under the conditions of this culture, an AhR binding and activation activity (see also FIGS. 14 and 15 and 16).

The expression of the messenger RNAs of vascular endothelial growth factors (VEGFs) and of their receptors is increased in skin exposed to TCDD. FIG. 8 shows the ratio (RT PCP) on fragments of human skin containing 1800 ppt of TODD, measured by gas chromatography/mass spectrometry, in comparison with the controls.

Contraction of chronic wounds and the development of epithelial healing with strips of keratinocytes was observed after application of a tryptophan gel generating, in the wound, factors capable of activating AhR (FIGS. 15-16). Also noted is thickening of the dermatoporotic skin around the wound which, in the opinion of the specialists, has a less atrophic and younger appearance. FIG. 9 is representative of a series of 10 cases of chronic wounds on legs exhibiting dermatoporosis.

EXAMPLE 3

Estrogenic Effect

The expression of the messenger RNAs of the various estrogen ESRR and ER, of the estrogen responsive finger protein ligase and of the estrogen-producing aromatase enzyme is increased in skin exposed to TCDD. FIG. 10*a* shows the RT PCR ratios on fragments of human skin containing 1800 ppt of TCDD, measured by gas chromatography/mass spectrometry, in comparison with the controls: exposing a man to high doses of TCDD significantly increases, in the skin, the expression of messenger RNAs of estrogen receptors and of associated proteins, and also of aromatase, thus corresponding to a state of hyperestrogenism. FIG. 10*b* shows that, in these skin fragments, there is a strong ectopic and focal expression of the ER-alpha receptor protein in the pilosebaceous structures, which indicates that the local induction of a state of hyperestrogenism by TCDD is focused on a skin structure which is known to be hormone-dependent. The immunohistochemistry reveals a strong and very focal expression of the estrogen receptor alpha, ERα, at the level of the pilosebaceous structures.

FIG. 11 shows the increase in the concentration of estradiol (E2) in human skin exposed to TCDD, determined by ELISA on fragments of human skin containing 1900 ppt of TCDD (measured by gas chromatography/mass spectrometry) in comparison with the controls (f<40: women under the age of 40; f>40: women over the age of 40; males 50 years old). These results demonstrate for the first time in humans the local induction by TCDD of a state of hyperestrogenism focused on a skin structure which is known to be hormone-dependent.

EXAMPLE 4

Defense Against Infection

As shown in FIG. 12, the colonization of human skin by staphylococcus sp (number of CFU, colony forming units, per $cm^2$) is very greatly decreased in the event of exposure to TCDD. This figure shows the values obtained on 4 samples taken 1 month apart from a human individual expressing more than 900 ppt of TCDD in the skin, measured by gas chromatography/mass spectrometry. The same effect is observed on *P. acnes* colonization, and illustrated in FIG. 13.

EXAMPLE 5

In Vitro Methods for Identifying Ligands According to the Invention

AhR activation tests

FIGS. 14, 15 and 16 show AhR activation in HEP G2 cells and normal human keratinocytes (NHKs) stably transfected with the lentivector plox-XRE TATA-Luc.

The Hep G2 cells are cultured in DMEM (Gibco)+10% fetal bovine serum+penicillin+streptomycin, the NHKs in keratinocyte SFM medium (Gibco)+penicillin+streptomycin. At D0, the Hep G2 cells are seeded into 12-well plates in a proportion of approximately 30 000 cells/$cm^2$. The NHKs are seeded into 6-well plates in a proportion of approximately 15 000 cells/$cm^2$. After 24 h, the medium is replaced with fresh medium and the cells are transduced with the lentivector plox-XRE TATA-Luc. After 48 h, the cells are subcultured and maintained in culture, and tested for their reactivity to TCDD.

The tests are carried out using the luciferase reporter assay system kit from Promega. At D0, the cells are seeded at a density of approximately 60% confluence, and then treated, at D1, with the test substance diluted to various concentrations in the appropriate culture medium. At D2, the cells are lysed in CLB buffer, and the lysate is clarified by centrifugation for 5 min at 10 000 g. The luciferase activity is measured in 20 microliters of lysate as recommended by the supplier, using the luminoskan luminometer (Thermo). After treatment for 24 h with 10 nM of TODD, a 100-fold induction of the luciferase activity is observed in the Hep G2-plox-XRE TATA-Luc cells and a 10-fold induction is observed in the NKK-plox-XRE TATA-Luc cells.

FIG. 14 shows the AhR activation in HEP G2 cells with various ligands according to the invention. The values represent the percentage activation compared to that obtained with 0.01 µM TODD, using the concentration, in µM, most active in the range tested for each substance. It is noted that ethyl β-carboline-3-carboxylate (B-CCE), tryptophan, rutaecarpine, hispidin and FICZ exhibit the greatest activities.

FIG. 15 shows, with the same representation, the activity of the same ligands on normal human keratinocytes. Similar results are noted.

Test for Potentiation by Bacterial Flora

FIG. 16 shows the AhR activation in HEP G2 cells with various extracts of common human skin bacteria in the presence of tryptophan (trp); F1: G+flora; F2: G+flora; PA: *P. acnes*; SE: *S. epidermidis*. The activation value 25.00 on the Y-axis corresponds to 1/6 of the AhR stimulation by 10 nM TCDD in this same system (157.00). It is seen that, in particular with P. acnes, an increase in the activation is observed with the addition of tryptophan. These observations illustrate the concept of AhR activation by tryptophan, partly by interaction with the surface flora.

CYP1A1 Activity Test

The tests are carried out using the P450-GLO assay kit from Promega. At D0, the cells are seeded at a density of approximately 60% confluence, and then treated at D1 with the test substance diluted to various concentrations in the appropriate culture medium. At D2, the CYP1A1 activity is measured as recommended by the supplier, using the nonlytic protocol on a cell monolayer. After treatment for 24 h with 10 nM of TODD, a 250-fold induction of the CYP1A1 activity was observed in the Hep G2 cells and a 20-fold induction was observed in the NHK cells, as shown in FIG. 17. FIG. 17 shows, likewise, the induction of this AhR-dependent biological activity with ligands according to the invention, said ligands being carvedilol, B-CCE and rutaecarpine.

As will be noted by those skilled in the art, the results of tests disclosed above illustrate a methodology for selection of molecules that are candidates for use in the production of a composition according to the invention.

What is claimed is:

1. A method of treating acne in a subject in need thereof which comprises topically applying to the subject a composition consisting of beta-naphthoflavone and a carrier.

2. The method of claim 1, wherein the composition is a lotion, gel, cream, ointment, foam or impregnated dressing.

3. The method of claim 1, wherein the acne is associated with *Propionibacterium acnes* present on facial skin.

4. The method of claim 1, wherein the composition is topically administered once a day.

* * * * *